United States Patent [19]

Higuchi et al.

[11] 3,956,490

[45] May 11, 1976

[54] ADMINISTRATION OF ALKALINE EARTH METAL SALTS OF SALICYLAMIDE

[75] Inventors: Takeru Higuchi, Lawrence, Kans.; Anwar A. Hussain, Lexington, Ky.

[73] Assignee: Interx Research Corporation, Lawrence, Kans.

[22] Filed: Mar. 11, 1975

[21] Appl. No.: 557,367

Related U.S. Application Data

[63] Continuation-in-part of Ser. No. 255,901, May 22, 1972, abandoned, which is a continuation of Ser. No. 22,049, March 23, 1970, abandoned.

[52] U.S. Cl. .................................. 424/233; 424/230
[51] Int. Cl.² ................. A61K 31/615; A61K 31/60
[58] Field of Search .......................... 424/233, 230

[56] References Cited
UNITED STATES PATENTS 2,158,091  5/1939  Stevens .............................. 424/233
3,064,038  11/1962  Adams ................................ 424/233
3,068,147  12/1962  Emele ................................ 424/233

OTHER PUBLICATIONS

Kakemi et al.–Chem. Abst. Vol. 56 (1962) p. 7933a.

Chem. Abst.–Vol. 59 (1963) p. 13234e.

*Primary Examiner*—Sam Rosen
*Attorney, Agent, or Firm*—Charles N. Blitzer

[57] ABSTRACT

Alkaline earth metal salts of salicylamide are administered in solid oral dosage forms with substantially improved analgesic, anti-inflammatory, antipyretic and sedative results as compared with salicylamide. Highest blood levels are obtained by administering enteric-coated salicylamide salt dosage forms.

11 Claims, No Drawings

ADMINISTRATION OF ALKALINE EARTH METAL SALTS OF SALICYLAMIDE

CROSS-REFERENCE TO RELATED APPLICATIONS

This application is a continuation-in-part application of our earlier copending application, Ser. No. 255,901, filed May 22, 1972, now abandoned, which in turn is a continuation application of our still earlier copending application, Ser. No. 22,049, filed Mar. 23, 1970, now abandoned.

BACKGROUND OF THE INVENTION

1. Field of the Invention

This invention relates to orally administrable dosage units for use as an analgesic, antipyretic, anti-inflammatory, or sedative.

2. Description of the Prior Art

Salicylamide is widely used in analgesic, anti-inflammatory, and antipyretic preparations. There are many conflicting reports, however, as to the efficacy of this drug. Salicylamide is a relatively insoluble drug, having a water solubility of only 0.2 percent at 30° C. When orally administered from tablets or capsules, a substantial amount of salicylamide fails to dissolve during passage through the gastrointestinal tract and can be recovered in the feces. Often as much as one-third of the drug is lost in this manner.

Additionally, a significant portion of the salicylamide which does go into solution is conjugated during absorption through the intestinal walls to its glucuronide and sulfate derivatives, neither of which has the desired pharmacological activity. Thus, very little of the salicylamide orally administered in solid dosage forms reaches the bloodstream in active form.

When administered intravenously, salicylamide elicits excellent analgesic, anti-inflammatory, antipyretic and sedative responses. The relative strength of these responses is dose dependent. Because intravenous administration is impractical for most conditions of use, a need remains for a means of orally administering effective amounts of salicylamide.

SUMMARY OF THE INVENTION

Accordingly, it is an object of this invention to provide a solid oral dosage form for use as an analgesic, anti-inflammatory, antipyretic, or sedative.

Another object of this invention is to provide a solid oral dosage form for effectively administering salicylamide.

In accomplishing these objects, one feature of this invention resides in an orally administrable dosage unit for use as an analgesic, antipyretic, anti-inflammatory, or sedative comprising a unit dosage amount of an alkaline earth metal salt of salicylamide in an orally acceptable solid pharmaceutical carrier.

Another feature of this invention resides in a dosage unit, as described above, having an enteric coating that resists solution in gastric fluid but disintegrates in the small intestine.

Other objects, features and advantages of this invention will become more apparent to those skilled in the art from the detailed description of the invention which follows.

DESCRIPTION OF THE INVENTION

In accordance with this invention, it has been found that oral administration of alkaline earth metal salts of salicylamide from solid dosage forms provides therapeutically effective blood levels of salicylamide, substantially higher than when salicylamide itself is administered. Dosage forms containing these salicylamide salts have greater usefulness as analgesics, antipyretics, anti-inflammatories, and sedatives than do similar dosage forms containing salicylamide.

Salts useful in the present invention can be represented by the formula:

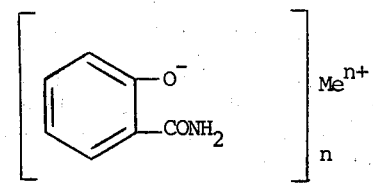

wherein Me is an alkaline earth metal cation of valence n and n is 2.

Various pharmaceutically acceptable alkaline earth metal salts of salicylamide can be orally administered. Of these, the magnesium and calcium salts are preferred. Best results are obtained with the calcium salt.

Two major problems with oral salicylamide administration, namely, insolubility and conjugation during absorption, have long been recognized. Both are improved upon by the present invention. Thus, alkaline earth metal salts of salicylamide dissolve substantially completely in the gastrointestinal tract and are available for absorption, eliminating the problem of the drug simply passing through the gastrointestinal tract. And, significantly, the greater availability of the drug to the wall of the small intestine can overcome the problem of inactivation by conjugation during absorption. This is especially true when the dosage unit is provided with an enteric coating that resists solution in gastric fluids but disintegrates in the small intestine. Through use of an enteric coating, the highly soluble salicylamide salt is presented to a relatively small area of the intestinal wall in high concentration. By presenting a quantity of drug higher than that which can be conjugated by the means available, the bulk of the salicylamide salt is absorbed in a free state. Thus, the large quantity of salicylamide salt presented to a small segment of the small intestine wall tends to overwhelm or swamp the inactivation mechanism.

Salicylamide salts can be effectively administered from various solid oral dosage forms, such as tablets, pills, powders, or capsules. These dosage forms can contain conventional additives such as diluents, binders, lubricants, disintegrators, and coloring agents. Typical diluents include dicalcium phosphate, calcium sulfate, lactose, kaolin, mannitol, dry starch, and powdered sugar. Typical binders include starch, gelatin, sugars, such as sucrose, molasses, and lactose, natural and synthetic gums such as acacia, sodium alginate, extract of Irish moss, carboxymethylcellulose, methylcellulose, and polyvinylpyrrolidone, polyethylene glycol, ethylcellulose, and waxes. Typical lubricants for use in these dosage forms include boric acid, sodium benzoate, sodium acetate, sodium chloride, leucine, and polyethylene glycol. Disintegrators which can be present include such agents as starch, methylcellulose, agar, bentonite, cellulose and wood products, alginic acid, guar gum, citrus pulp, carboxymethylcellulose, and sodium lauryl sulfate. If desired, conventional pharmaceutically acceptable dyes can be incorporated in the dosage unit.

Best results are obtained when the oral dosage unit has an enteric coating. Any enteric coating can be employed so long as it will protect the salicylamide salt from dissolution as it passes through the stomach and disintegrates in the small intestine. Usually, the enteric coating material is a cellulose lower fatty acid phthalate, particularly cellulose acetate phthalate. However, other cellulose derivatives can be used. For example, cellulose ethers or mixed ether esters can be substituted for the cellulose esters. Thus, among the enteric coating materials which can be used are the materials formed by reacting cellulose acetate, cellulose propionate, cellulose acetate butyrate, ethyl cellulose, butylcellulose, etc., with phthalic or maleic anhydrides or the like in the presence of a tertiary organic base. The only limitation on the enteric coating is that it shall preserve the salicylamide salt from dissolution until it reaches the small intestine. Therefore, in addition to the coatings described above, one can use any of the conventional enteric coatings such as shellac and others described in "Remmington's Pharmaceutical Sciences", Thirteenth Edition, Mack Publishing Company, 1965, pp 604–605.

The solid oral dosage form, whether tablets, capsules, pills or powders, is prepared in the conventional manner. When an enteric coating is used, the dosage form can be dipped, sprayed, etc., with the coating material until a coating of the desired thickness is obtained. Those skilled in the art are well aware of the standard techniques which can be used to prepare these dosage forms and to provide them with an enteric coating.

Salicylamide salts are administered in the same unit dose amounts conventionally used with salicylamide. In general, each dosage contains from 50 to 750 milligrams of the salicylamide salt. Typically, about 300 milligrams are incorporated in the dosage unit.

Salicylamide salts can be administered in conjunction with other drugs to obtain enhanced efficacy. When this is done, the amount of the salicylamide salt in the dosage unit can vary from the ranges previously set forth and the amount to be administered can be readily determined by those skilled in the art. Typical of other drugs that can be combined with the alkaline earth metal salts of salicylamide to provide a combination dosage unit are: phenacetin, aspirin, sodium salicylate, caffeine, acetaminophen, scopolamine, phenylephrine hydrochloride, glycerol guaiacolate, chlorpheniramine maleate, belladonna alkaloids, dextromethorphan hydrobromide, ephedrine hydrochloride, and phenylpropanolamine hydrochloride.

Unexpectedly good results are obtained when a salicylamide salt is combined with an alkali or alkaline earth metal salt of acetaminophen having the formula:

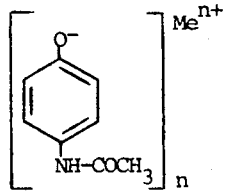

wherein Me is an alkali or alkaline earth metal cation of valence $n$ and $n$ is 1 or 2. Such dosage forms, containing salts of both drugs, are prepared in a conventional manner, as described above. The mole ratio of the salicylamide salt to the acetominophen salt can vary in the range of 0.25:1 to 4:1 but the total unit dosage amount of drug should be from 50 to 750 milligrams. Though one can depart from these ranges, the synergistic effect, resulting in higher blood levels of drug, is not present. These combination dosage forms too benefit from enteric coating.

In a specific example of the invention, calcium salicylamide was prepared by incrementally adding salicylamide (10 grams, 0.073 mole) to 1 Normal calcium hydroxide (70 milliliters, 70 milliequivalents) and stirring the mixture for one hour. Thereafter, the reaction product was extracted with chloroform and ether to remove excess salicylamide. Water was removed from the aqueous layer by spin evaporation under vacuum, depositing the calcium salicylamide product. The solid product was purified by dissolving in methyl alcohol containing anhydrous sodium sulfate. The methyl alcohol solution was filtered and spin evaporated in vacuo leaving the purified white solid calcium salicylamide product.

Other alkaline earth metal salts of salicylamide can be prepared in a similar manner.

To compare the dissolution rates of calcium salicylamide and salicylamide, 300 milligram half-inch diameter tablets having a thickness of 1 millimeter, were prepared in a Carver Press at 10 pounds per square inch pressure. When placed in simulated gastric fluid (400 milliliters, 0.1 Normal HCl) at 37° C in a round bottom flask magnetically stirred at 60 RPM, the results set forth in the following table were obtained.

| ELAPSED TIME | PERCENT DISSOLVED CALCIUM SALICYLAMIDE | SALICYLAMIDE |
| --- | --- | --- |
| 1 min. | 15 | <1 |
| 2 min. | 35 | <1 |
| 5 min. | 70 | 1 |
| 11 min. | 98 | 1 |
| 20 min. | 100 | 2 |
| 1 hr. | — | 5 |
| 2 hr. | — | 20 |
| 4 hr. | — | 35 |
| 8 hr. | — | 60 |
| 20 hr. | — | 85 |
| 40 hr. | — | 97 |
| 44 hr. | — | 100 |

When tablets prepared in an identical manner were tested under the same conditions in simulated intestinal fluid (6.80 parts monobasic potassium phosphate, 1.52 parts sodium hydroxide, 1000 parts distilled water) of pH 7.5, the following results were obtained.

| ELAPSED TIME | PERCENT DISSOLVED CALCIUM SALICYLAMIDE | SALICYLAMIDE |
| --- | --- | --- |
| 1 min. | 16.0 | — |
| 5 min. | 70.0 | — |
| 10 min. | 98.0 | — |
| 15 min. | 99.0 | — |
| 20 min. | 100.0 | — |
| 25 min. | — | — |
| 30 min. | — | 5.0 |
| 4 hr. 35 min. | — | 25.0 |
| 17 hr. 5 min. | — | 75.0 |
| 24 hr. 10 min. | — | 90.0 |
| 26 hr. 25 min. | — | 95.0 |

| ELAPSED TIME | PERCENT DISSOLVED | |
|---|---|---|
| | CALCIUM SALICYLAMIDE | SALICYLAMIDE |
| 46 hr. 30 min. | — | 100.0 |

Conventionally prepared tablets containing alkaline earth metal salts of salicylamide provide substantially higher blood levels, in mammals, of salicylamide than do identical tablets containing salicylamide itself. Thus, this invention provides solid dosage forms with significantly improved usefulness as analgesics, antipyretics, anti-inflammatories, and sedatives.

While the invention has been described and pointed out with reference to certain preferred embodiments thereof, those skilled in the art will appreciate that various changes and modifications and substitutions can be made without departing from the spirit of the invention. It is intended, therefore, that the invention be limited only by the scope of the claims which follow.

What we claim is:

1. The method of obtaining analgesia, lowering body temperature, treating inflammation, or obtaining sedation in a mammalian organism, which method comprises administering to such organism a unit dosage analgesically, antipyretically, anti-inflammatorily, or sedatively effective amount of an alkaline earth metal salt of salicylamide in a pharmaceutically acceptable carrier.

2. The method as defined by claim 1, wherein the unit dosage amount is orally administered.

3. The method as defined by claim 2, wherein the unit dosage amount is orally administered in solid form.

4. The method as defined by claim 1, wherein the unit dosage amount further comprises an alkali or alkaline earth metal salt of acetaminophen, the mole ratio of said alkaline earth metal salt of salicylamide to said acetaminophen salt being in the range of from about 0.25:1.0 to 4.0:1.0.

5. The method as defined by claim 3, wherein the solid, unit dosage has an enteric coating that resists solution in gastric fluid but disintegrates in the small intestine.

6. The method as defined by claim 1, wherein the unit dosage amount contains from about 50 to 750 milligrams of the alkaline earth metal salt of salicylamide.

7. The method of claim 1, wherein said alkaline earth metal salt is calcium.

8. An orally administrable dosage unit for use as an analgesic, antipyretic, anti-inflammatory, or sedative, comprising a solid oral dosage form tablet, pill, powder, or capsule which comprises a shaped, orally administrable analgesically, antipyretically, anti-inflammatorily or sedatively effective unit dosage amount of a purified, solid alkaline earth metal salt of salicylamide in an orally acceptable, solid pharmaceutical carrier.

9. The dosage unit of claim 8, wherein said alkaline earth metal salt is calcium.

10. The dosage unit of claim 8, further comprising an alkali or alkaline earth metal salt of acetaminophen, the mole ratio of said alkaline earth metal salt of salicylamide to said acetaminophen salt being in the range of from about 0.25:1.0 to 4.0:1.0.

11. The dosage unit of claim 8, wherein said unit has an enteric coating that resists solution in gastric fluid but disintegrates in the small intestine.

* * * * *